(12) United States Patent
Yamamoto et al.

(10) Patent No.: US 11,471,819 B2
(45) Date of Patent: Oct. 18, 2022

(54) GAS REFINING APPARATUS, GAS REFINING METHOD, PROPENE MANUFACTURING APPARATUS, AND PROPANE MANUFACTURING APPARATUS

(71) Applicant: TAIYO NIPPON SANSO CORPORATION, Tokyo (JP)

(72) Inventors: Kazuo Yamamoto, Tokyo (JP); Hiroyuki Ono, Tokyo (JP); Takafumi Tomioka, Tokyo (JP)

(73) Assignee: TAIYO NIPPON SANSO CORPORATION, Tokyo (JP)

( * ) Notice: Subject to any disclaimer, the term of this patent is extended or adjusted under 35 U.S.C. 154(b) by 34 days.

(21) Appl. No.: 16/962,030

(22) PCT Filed: Feb. 15, 2019

(86) PCT No.: PCT/JP2019/005504
§ 371 (c)(1),
(2) Date: Jul. 14, 2020

(87) PCT Pub. No.: WO2019/160074
PCT Pub. Date: Aug. 22, 2019

(65) Prior Publication Data
US 2020/0398210 A1    Dec. 24, 2020

(30) Foreign Application Priority Data
Feb. 16, 2018   (JP) .............................. JP2018-026432

(51) Int. Cl.
*B01D 53/04*    (2006.01)
*C07C 7/12*     (2006.01)
(Continued)

(52) U.S. Cl.
CPC .............. *B01D 53/047* (2013.01); *C07C 7/12* (2013.01); *C07C 9/08* (2013.01);
(Continued)

(58) Field of Classification Search
CPC ............ B01D 53/047; B01D 2253/102; B01D 2253/104; B01D 2253/108;
(Continued)

(56) References Cited

U.S. PATENT DOCUMENTS

| 4,732,577 | A | 3/1988 | Koizumi et al. |
| 4,864,071 | A * | 9/1989 | Hirai ........................ C07C 7/12 |
| | | | 585/829 |
| 2014/0148634 | A1 | 5/2014 | Park et al. |

FOREIGN PATENT DOCUMENTS

| CN | 1445205 A | 10/2003 |
| CN | 104607000 A | 5/2015 |

(Continued)

OTHER PUBLICATIONS

JP2012171851A_English Translation (Year: 2012).*
(Continued)

*Primary Examiner* — Youngsul Jeong
(74) *Attorney, Agent, or Firm* — Nixon & Vanderhye P.C.

(57) ABSTRACT

An object of the present invention is to provide a gas refining apparatus which can produce a product gas with high purity and high yield at low cost and can produce a plurality of types of gas as a product gas without changing an adsorbent, and the present invention provides a gas refining apparatus (10) including a first derivation line (L3) connected to the second adsorption towers (2a, 2b) and through which the first gas flows, a second derivation line (L4) connected to the second adsorption towers (2a and 2b) and through which the second gas flows, a regeneration line (L5) connected to the first adsorption towers (1a, 1b), through which a regeneration gas for regenerating a first adsorbent in the first adsorption towers (1a, 1b) flows, and a pump (P) provided in the second derivation line (L4) and configured to desorb the second gas from a second adsorbent in the second adsorption
(Continued)

towers (2a and 2b), and the regeneration line (L5) is connected to each of the first derivation line (L3) and the second derivation line (L4).

8 Claims, 2 Drawing Sheets

(51) Int. Cl.
*B01D 53/047* (2006.01)
*C07C 9/08* (2006.01)
*C07C 11/06* (2006.01)

(52) U.S. Cl.
CPC .. *B01D 2253/102* (2013.01); *B01D 2253/104* (2013.01); *B01D 2253/108* (2013.01); *B01D 2253/116* (2013.01); *B01D 2256/24* (2013.01); *B01D 2257/504* (2013.01); *B01D 2259/40007* (2013.01); *C07C 11/06* (2013.01)

(58) Field of Classification Search
CPC .......... B01D 2253/116; B01D 2256/24; B01D 2257/504; B01D 2259/40007; C07C 7/12; C07C 9/08; C07C 11/06
See application file for complete search history.

(56) References Cited

FOREIGN PATENT DOCUMENTS

| JP | 60-97022 | | 5/1985 | |
|---|---|---|---|---|
| JP | 62-117612 | A | 5/1987 | |
| JP | 62-241524 | | 10/1987 | |
| JP | 64-3003 | | 1/1989 | |
| JP | 1-307426 | A | 12/1989 | |
| JP | 4-126512 | A | 4/1992 | |
| JP | 11-199206 | | 7/1999 | |
| JP | 2006-508020 | | 3/2006 | |
| JP | 2012-171851 | | 9/2012 | |
| JP | 2012171851 | A * | 9/2012 | ............ B01D 53/04 |
| WO | 03/080548 | | 10/2003 | |

OTHER PUBLICATIONS

Office Action dated Aug. 30, 2021 issued in Chinese Application No. 201980006109.7 with English translation (22 pages).
Suzuki, et al., "Pressure swing cycle system", Kodansha Ltd., 1983, 6 pages with Partial Translation.
International Search Report for PCT/JP2019/005504 dated May 7, 2019, 4 pages.
Notice of Allowance dated Jan. 25, 2022 in Japanese Application No. 2018-026432 with English translation (4 pages).

* cited by examiner

GAS REFINING APPARATUS, GAS REFINING METHOD, PROPENE MANUFACTURING APPARATUS, AND PROPANE MANUFACTURING APPARATUS

This application is the U.S. national phase of International Application No. PCT/JP2019/005504 filed Feb. 15, 2019 which designated the U.S. and claims priority to JP Patent Application No. 2018-026432 filed Feb. 16, 2018, the entire contents of each of which are hereby incorporated by reference.

FIELD OF THE INVENTION

The present invention relates to a gas refining apparatus, a gas refining method, a propene manufacturing apparatus, and a propane manufacturing apparatus.

DESCRIPTION OF RELATED ART

Distillation and the like are used as a technique for refining components contained in a mixed gas. However, in a case of refining a component of a mixed gas containing a plurality of compounds having similar chemical properties such as propane and propene, the use of distillation has the disadvantage of increasing the scale of the apparatus and increasing the equipment cost.

In the production of industrial gas, as an apparatus for refining a raw material gas containing an object to be removed to obtain a product gas, an apparatus of a pressure swing adsorption system, so-called PSA apparatus has been known (Patent Document 1. Non-Patent Document 1, and the like). As the PSA apparatus, there has been also known an apparatus which performs a PSA method for gas obtained by separating an object from a raw material gas by a PSA method a plurality of times (Patent Document 2 and the like).

Since the PSA apparatus uses an adsorbent which adsorbs an object to be removed, even a gas mixture containing a plurality of compounds having similar chemical properties can separate a target gas with a relatively small-scale apparatus.

PRIOR ART DOCUMENTS

Patent Documents

Patent Document 1: Japanese Unexamined Patent Application, First Publication No. H11-199206
Patent Document 2: Japanese Unexamined Patent Application, First Publication No. S60-97022

Non-Patent Documents

Non-Patent Document 1: Written by Kenichiro Suzuki, Pressure swing cycle system, 1983, published by Kodansha Ltd.

DISCLOSURE OF THE INVENTION

Problem to be Solved by the Invention

However, in the conventional PSA apparatus, it is difficult to remove 70% or more of an object to be removed from a raw material gas and to produce each of a plurality of compounds having similar chemical properties as a product gas with a recovery rate of 90% or more.

For example, in the apparatus disclosed in Patent Document 1, when the adsorbent in the adsorption tower is regenerated, a part of a product gas is used as a regeneration gas, so that the recovery rate of the product gas is reduced and the recovery amount of the product gas is also reduced.

Non-Patent Document 1 discloses an apparatus which regenerates an adsorbent using a vacuum pump. In the apparatus described in Non-Patent Document 1, if the adsorbent is regenerated using a vacuum pump without using part of the product gas as the regenerating gas, the recovery amount of the product gas does not easily decrease. However, if a vacuum pump is used like the apparatus described in Non-Patent Document 1, equipment costs, power consumption, and maintenance cost of the apparatus increase, and manufacturing costs increase.

On the other hand, in the production of a product gas using a PSA apparatus, it is sometimes required to recover components adsorbed on the adsorbent in the adsorption tower as a product gas. However, in the apparatus disclosed in Patent Document 2, in order to recover the components adsorbed on the adsorbent as a product gas in high yield, it is necessary to change the type of the adsorbent in the adsorption tower. PSA apparatus remodeling costs such as changing the type of adsorbent occur, which is disadvantageous in terms of cost.

The present invention has been made in view of the above circumstances, and an object of the present invention is to provide a gas refining apparatus and a gas refining method which can obtain a product gas with high purity and high yield at low cost and can produce multiple types of gas as the product gas without changing the adsorbent.

In addition, the present invention has been made in view of the above circumstances, another object of the present invention is to particularly provide a propene manufacturing apparatus and a propane manufacturing apparatus.

Means to Solve the Problem

In order to solve the problems, the present invention provides the following gas refining apparatuses, gas refining methods, propene manufacturing apparatus and propane manufacturing apparatus.

[1] A gas refining apparatus for refining a product gas from a raw material gas containing a first gas and a second gas by a pressure swing adsorption method, wherein the gas refining apparatus includes: a first adsorption tower having a first adsorbent for adsorbing gas other than the first gas and the second gas; a second adsorption tower having a second adsorbent for adsorbing the second gas; a connection line which connects a secondary side of the first adsorption tower and a primary side of the second adsorption tower, and through which the first gas and the second gas flow; a first derivation line connected to the secondary side of the second adsorption tower and through which the first gas flows; a second derivation line connected to the primary side of the second adsorption tower and through which the second gas flows; a regeneration line connected to the secondary side of the first adsorption tower and through which a regeneration gas for regenerating the first adsorbent flows; and a suction apparatus provided in the second derivation line and configured to desorb the second gas from the second adsorbent; and the regeneration line is connected to each of the first derivation line and the second derivation line.

[2] The gas refining apparatus according to [1], wherein the gas refining apparatus further includes a first recovery line branched from the first derivation line, and a second recovery line branched from the second derivation line, an on-off valve is provided in each of the first derivation line, the second derivation line, the first recovery line, and the second recovery line, and by switching the open/close state of the on-off valve, one of the first gas and the second gas is selected and recovered as the product gas.

[3] A gas refining method by a pressure swing adsorption system using the gas refining apparatus according to [1] or [2], wherein the gas refining method includes: a step of causing the first adsorbent to adsorb gas other than the first gas and the second gas, which is contained in the raw material gas, a step of supplying the first gas and the second gas from the first adsorption tower into the second adsorption tower; a step of adsorbing the second gas on the second adsorbent, then desorbing the second gas from the second adsorbent, and recovering the second gas desorbed from the second adsorbent as the product gas through the second derivation line; and a step of introducing the first gas from the first derivation line into the regeneration line.

[4] A gas refining method by a pressure swing adsorption system using the gas refining apparatus according to [1] or [2], wherein the gas refining method includes: a step of causing the first adsorbent to adsorb gas other than the first gas and the second gas, which is contained in the raw material gas, a step of supplying the first gas and the second gas from the first adsorption tower into the second adsorption tower; a step of adsorbing the second gas on the second adsorbent, then recovering the first gas from the first derivation line as the product gas, and a step of desorbing the second gas from the second adsorbent, and introducing the second gas desorbed from the second adsorbent from the second derivation line into the regeneration line.

[5] A propene manufacturing apparatus which produces propene from a raw material gas containing propane and propene by a pressure swing adsorption method, wherein the propene manufacturing apparatus includes: a first adsorption tower having a first adsorbent for adsorbing gas other than propane and propene; a second adsorption tower having a second adsorbent for adsorbing propene, a connection line which connects a secondary side of the first adsorption tower and a primary side of the second adsorption tower, and through which propane and propene flow; a first derivation line connected to a secondary side of the second adsorption tower and through which propane flows, a second derivation line connected to the primary side of the second adsorption tower and through which propene flows, a regeneration line connected to the secondary side of the first adsorption tower and through which propane for regenerating the first adsorbent flows; and a suction apparatus provided in the second derivation line and configured to desorb propene from the second adsorbent; the regeneration line is connected to each of the first derivation line and the second derivation line, propane is introduced from the first derivation line into the regeneration line and the propene is recovered from the second derivation line.

[6] A propane manufacturing apparatus which produces propane from a raw material gas containing propane and propene by a pressure swing adsorption method, wherein the propane manufacturing apparatus includes: a first adsorption tower having a first adsorbent for adsorbing gas other than propane and propene; a second adsorption tower having a second adsorbent for adsorbing propene, a connection line which connects a secondary side of the first adsorption tower and a primary side of the second adsorption tower, and through which propane and propene flow; a first derivation line connected to a secondary side of the second adsorption tower and through which propane flows, a second derivation line connected to the primary side of the second adsorption tower and through which propene flows, a regeneration line connected to the secondary side of the first adsorption tower and through which propene for regenerating the first adsorbent flows; and a suction apparatus provided in the second derivation line and configured to desorb propene from the second adsorbent; the regeneration line is connected to each of the first derivation line and the second derivation line, propene is introduced from the second derivation line into the regeneration line and propane is recovered from the first derivation line.

Effects of the Invention

According to the present invention, a product gas can be obtained with high purity and high yield at low cost, and a plurality of types of gas can be manufactured as product gas without changing the adsorbent.

DETAILED DESCRIPTION OF THE INVENTION

Figure 1:
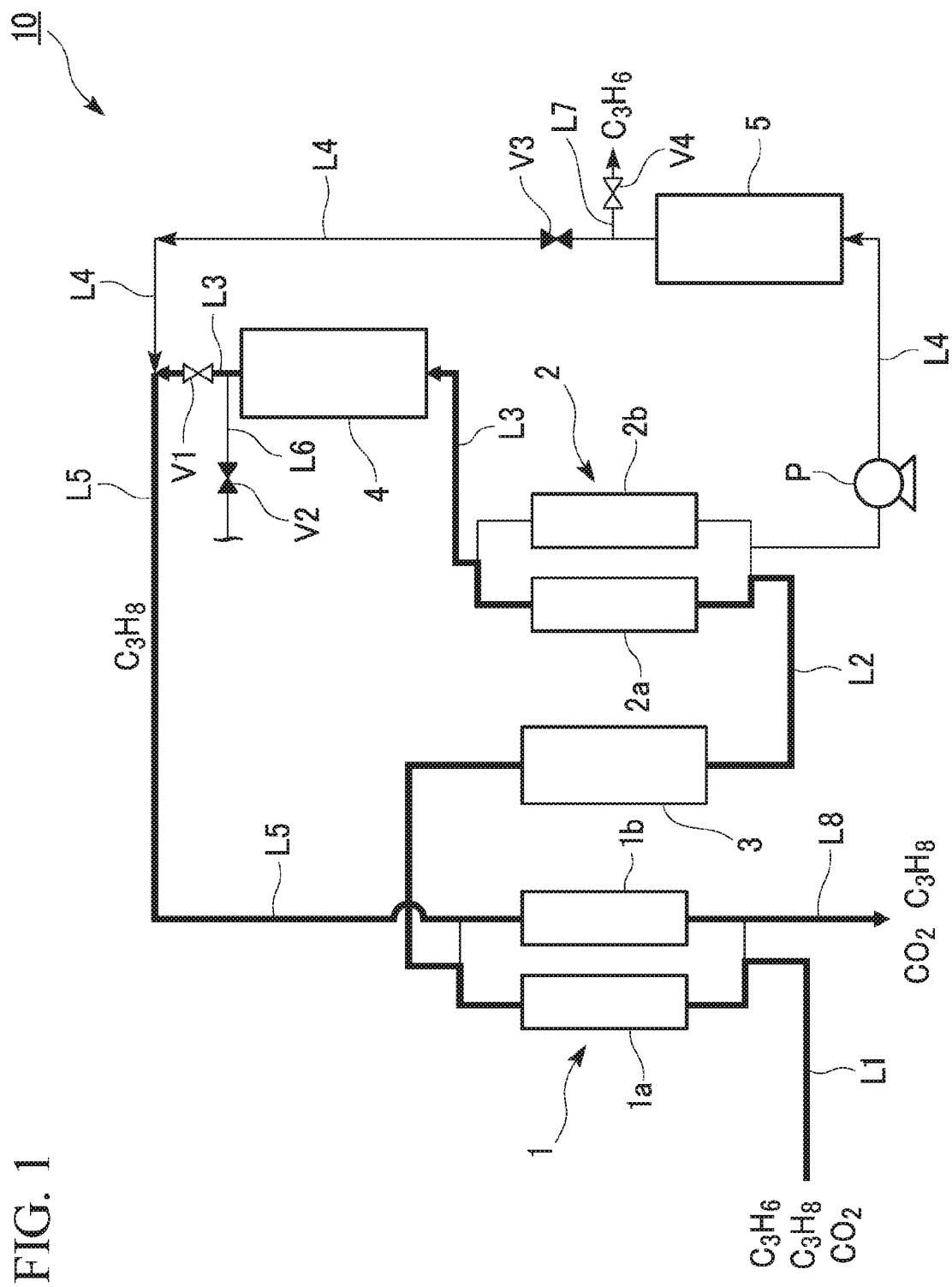
FIG. 1 is a schematic diagram showing an example of a gas refining apparatus of a first embodiment according to the present invention.

The meaning of the following terms in the present description is as follows.

"PSA" is an abbreviation for Pressure Swing Adsorption. In the present description, the pressure swing adsorption method is referred to as "PSA method", and an apparatus for refining gas by the PSA method is referred to as "PSA apparatus".

The "regeneration" of an adsorbent means that an adsorbent on which an object to be removed has been adsorbed is returned to a state in which the object to be removed can be adsorbed again.

The "regeneration gas" means gas which is supplied into an adsorption tower having an adsorbent to be regenerated to regenerate the adsorbent.

The "regeneration exhaust gas" means gas which is discharged from an adsorption tower having an adsorbent to be regenerated, and used for regenerating the adsorbent.

Hereinafter, an embodiment according to the present invention will be described in detail with reference to the drawings. In the drawings used in the following description, in order to make the characteristics easy to understand, the characteristic portions may be shown in an enlarged manner for convenience, and the dimensional ratios and the like of the components are not necessarily the same as the actual ones.

<Gas Refining Apparatus>

A gas refining apparatus of the present embodiment is an apparatus for refining a product gas from a raw material gas including a first gas, a second gas, and an object to be removed.

The first gas, the second gas, and the object to be removed are not particularly limited. Specific examples of the first gas and the second gas include hydrocarbons such as ethane, ethylene, propane, propene, butane, and butene. Examples of the object to be removed include nitrogen, oxygen, argon, water vapor, methane, carbon monoxide, and carbon dioxide.

The combination of the first gas and the second gas may be a combination of at least one selected from the specific examples. Among them, even if a combination of compounds having similar chemical or physical properties is selected, such as a combination of ethane and ethylene, a combination of propane and propene, and a combination of butane and butene, the effect of the present invention can be obtained.

In the following embodiment, a case in which the raw material gas includes propane (first gas) and propene (second gas), and carbon dioxide as an object to be removed will be described as an example.

The gas refining apparatus of the present embodiment is a PSA apparatus. Therefore, in the following embodiments, the description of the configuration of the pressure reducing line and the pressure equalizing line provided in the general PSA apparatus, and the on-off valves and the like provided in these lines (that is, configuration with low relevance to the features of the present invention) is omitted and the illustration is also omitted. The gas refining apparatus of the present embodiment may or may not include these configurations, such as those of a typical PSA apparatus.

FIG. 1 is a schematic diagram showing an example of a gas refining apparatus 10 according to the present embodiment. As shown in FIG. 1, the gas refining apparatus 10 includes a first PSA unit 1, a second PSA unit 2, a first tank 3, a second tank 4, a third tank 5, a raw material line L1, and a connection line L2, a first derivation line L3, a second derivation line L4, a regeneration line L5, a first recovery line L6, a second recovery line L7, and a regeneration exhaust gas line L8.

Each component of the gas refining apparatus 10 will be described in detail below.

The first PSA unit 1 separates an object to be removed from a raw material gas. The first PSA unit 1 has a first adsorption tower 1a and a first adsorption tower 1b.

The first adsorption towers 1a and 1b have basically the same configuration, and have a hollow cylindrical shape. The first adsorption towers 1a and 1b have a first adsorbent inside. In the present embodiment, the first adsorbent is not particularly limited as long as it can adsorb an object to be removed (in the present embodiment, carbon dioxide; hereinafter, referred to as carbon dioxide). As the first adsorbent, an adsorbent containing molecular sieve carbon, amine-supported alumina, or the like is preferable.

The raw material line L1 is a line for supplying the raw material gas into the first adsorption towers 1a and 1b. The raw material line L1 is connected to the primary side (upstream side) of the first adsorption towers 1a and 1b.

The connection line L2 is a line for deriving gas including the first gas (propane ($C_3H_8$) in the present embodiment, hereinafter referred to as propane) and the second gas (propene ($C_3H_6$) in the present embodiment; hereinafter, referred to as propene) from the first PSA unit 1 into the second PSA unit 2. The connection line L2 connects the secondary side (downstream side) of the first adsorption tower 1a, 1b and the primary side (upstream side) of the second adsorption tower 2a, 2b. Specifically, the connection line L2 has a branched first end connected to each of the secondary sides of the first adsorption towers 1a and 1b, and a branched second end connected to the primary sides of the second adsorption towers 2a and 2b.

The first tank 3 is provided in the connection line L2. The first tank 3 is a tank for storing gas derived from the first PSA unit 1. Thereby, the gas containing propane and propene can be stably supplied from the first PSA unit 1 into the second PSA unit 2, and the fluctuation of the flow rate of the gas containing propane and propene can be reduced.

The second PSA unit 2 separates propane and propene. The second PSA unit 2 has a second adsorption tower 2a and a second adsorption lower 2b. The second adsorption towers 2a and 2b have basically the same configuration, and have a hollow cylindrical shape. The second adsorption towers 2a, 2b have a second adsorbent inside. In the present embodiment, the second adsorbent is not particularly limited as long as it can adsorb propene. As the second adsorbent, an adsorbent containing zeolite, silver ions-supported activated carbon, molecular sieve carbon and the like is preferable.

The first derivation line L3 is a line through which propane derived from the secondary side of the second PSA unit 2 flows. The first derivation line L3 has a branched first end connected to each of the secondary sides of the second adsorption towers 2a and 2b, and a second end connected to the regeneration line L5.

The first derivation line L3 is provided with the second tank 4 and an on-off valve V1 in this order from the primary side.

The first recovery line L6 is a line branched from the first derivation line L3. Specifically, the first recovery line L6 is branched off from the first derivation line L3 between the second tank 4 and the on-off valve V1. The first recovery line L6 is provided with an on-off valve V2. The first recovery line L6 is a line for recovering propane as the product gas.

The second tank 4 is a tank for storing propane derived from the second PSA unit 2. Thereby, apart of the propane separated in the second PSA unit 2 can be stably supplied from the second tank 4 into the first PSA unit 1 via the first derivation line L3 and the regeneration line L5. As a result, fluctuation of the flow rate of propane used as the regeneration gas for the first adsorbent can be reduced.

The second derivation line L4 is a line through which propene derived from the primary side of the second PSA unit 2 flows. The second derivation line L4 has a branched first end connected to each of the primary sides of the second adsorption towers 2a and 2b, and a second end connected to the regeneration line L5.

The second derivation line L4 is provided with a pump P, a third tank 5, and an on-off valve V3 in this order from the primary side.

The second recovery line L7 is a line branched from the second derivation line L4. Specifically, the second recovery line L7 is branched off from the second derivation line L4 between the third tank 5 and the on-off valve V3. The second recovery line L7 is provided with an on-off valve V4. The second recovery line L7 is a line for recovering propene as the product gas.

The pump P is an example of a suction apparatus which desorbs propene from the second adsorbent when propene is adsorbed on the second adsorbent. Accordingly, propene can be desorbed from the second adsorbent without supplying a part of the propane separated by the second PSA unit 2 as the regeneration gas for the second adsorbent into the second adsorption towers 2a and 2b.

The third tank 5 is a tank for storing propene derived from the second PSA unit 2. Thereby, a part of the propene separated in the second PSA unit 2 can be stably supplied from the third tank 5 into the first PSA unit 1 via the second derivation line LA and the regeneration line L5. As a result, fluctuation of the flow rate of propene used as the regeneration gas for the first adsorbent can be reduced.

The regeneration line L5 is a line for supplying the regeneration gas for the first adsorbent into the first adsorption towers 1a and 1b.

The regeneration line L5 has a first end connected to each of the second ends of the first derivation line L3 and the second derivation line LA, and a branched second end connected to each of the secondary sides of the first adsorption towers 1a and 1b. Thereby, either propane or propene can be supplied into the first adsorption towers 1a and 1b as the regeneration gas for the first adsorbent.

The regeneration exhaust gas line L8 is a line for discharging the regeneration exhaust gas from the first PSA unit 1. The regeneration exhaust gas line L8 is connected to the primary side of the first adsorption towers 1a, 1b. However, in FIG. 1, the connection between the regeneration exhaust gas line L8 and the first adsorption tower 1a is omitted for simplification.

Effects

In the gas refining apparatus of the present embodiment described above, since the first adsorbent adsorbs gas other than the first gas and the second gas, the purity of the product gas is increased.

In addition, since the regeneration line is connected to each of the first and second derivation lines, of the first gas and the second gas, the gas which is recovered as the product gas is not used as the regeneration gas, and the gas which is not recovered as the product gas can be supplied as the regeneration gas into the first adsorption tower. Specifically, in the gas refining apparatus of the present embodiment, when recovering the first gas (propane), the second gas (propene) can be supplied into the first adsorption tower as the regeneration gas. As a result, the first adsorbent can be regenerated without providing a vacuum pump in the regenerating exhaust gas line, the equipment costs of the apparatus can be kept low, and the recovery amount and the recovery rate of the gas to be recovered as the product gas can be increased.

Furthermore, since the first derivation line and the second derivation line are provided, the gas derived as the product gas from the second adsorption tower can be selected, and the gas to be recovered as the product gas can be easily changed without modification of the apparatus such as a change in the adsorbent. Specifically, when recovering the second gas (propene), the first gas (propane) can be supplied into the first adsorption tower as the regeneration gas.

In particular, according to the gas refining apparatus, as in the present embodiment, from the raw material gas containing a plurality of types of gas having similar chemical properties such as propane and propene, and the object to be removed such as carbon dioxide, each of propane and propene can be recovered as the product gas at the recovery rate of 90% or more, and 70% or more of the removal target in the raw material gas can be separated.

The gas refining apparatus 10 can be used as a propane manufacturing apparatus or a propene manufacturing apparatus because the gas refining apparatus 10 selects either propane or propene and recovers the product gas by switching the open/close state of the on-off valves V1 to V4.

<Gas Refining Method>

Hereinafter, a gas refining method of the present embodiment using the gas refining apparatus 10 above will be described. The gas refining method of the present embodiment is a gas refining method using the PSA system. Therefore, in the following embodiments, description of operations such as depressurization and pressure equalization performed in a general PSA gas refining method (that is, low relevance to the features of the present invention) will be omitted.

In the embodiment described below, a case in which the raw material gas is supplied into the first adsorption tower 1b, gas other than propane and propene is adsorbed to the first adsorbent in the first adsorption tower 1b, and propane and propene are supplied from the first adsorption tower 1b into the second adsorption tower 2b, and propene is adsorbed to the second adsorbent in the second adsorption tower 2b will be described as an example.

That is, in the following embodiment, description of the gas refining method will be started from a state in which carbon dioxide is adsorbed on the first adsorbent in the first adsorption tower 1b, propane is stored in the second tank 4, and propene is adsorbed on the second adsorbent in the second adsorption tower 2b.

First Embodiment

Hereinafter, the first embodiment will be described with reference to FIG. 1 as an example in which propene is recovered as the product gas. That is, in the first embodiment described below, the gas refining apparatus 10 is a propene manufacturing apparatus. In FIG. 1, a thick line means a line in which propane flows.

As shown in FIG. 1, the on-off valves V1 and V4 are opened, and the on-off valves V2 and V3 are closed. In this state, the raw material gas is supplied into the first adsorption tower 1a, and carbon dioxide is adsorbed on the first adsorbent in the first adsorption tower 1a. Thereby, carbon dioxide is removed from the raw material gas.

Next, gas containing propane and propene is derived from the first PSA unit 1 into the second PSA unit 2. That is, propane and propene are supplied from the first adsorption tower 1a into the second adsorption tower 2a. Propene is adsorbed on the second adsorbent in the second adsorption tower 2a, and propane is derived out into the first derivation line L3. Thereby, propane and propene are separated.

In the first embodiment, propene is desorbed from the second adsorbent in the second adsorption tower 2b, then recovered as the product gas from the second derivation line L4, and propane is introduced from the first derivation line L3 into the regeneration line L5.

That is, the propene desorbed from the second adsorbent in the second adsorption tower 2b passes through the second derivation line L4 and the second recovery line L7 in this order, and is recovered as the product gas. In addition, by introducing the propane separated in the second PSA unit 2 from the first derivation line L3 into the regeneration line L5, the propane can be used as the regeneration gas for the first adsorbent in the first adsorption tower 1b. As a result, carbon dioxide is desorbed from the first adsorbent in the first adsorption tower 1b, and the gas containing propane and carbon dioxide flows through the regeneration exhaust gas line L8.

When desorbing propene from the second adsorbent, it is preferable not to introduce the propane from the second adsorption tower into the second derivation line L4. As a result, the propane is less likely to be mixed into propene, which is the product gas, and the purity of the propene can be further increased. As a method of desorbing the propene from the second adsorbent, a method of using the pump P and sucking the inside of the second adsorption tower 2b through the second derivation line L4 is exemplified.

Effects

In the gas refining method of the first embodiment described above, propene is recovered as the product gas. Propane is not the product gas. By using propane (ie, the first gas) for regeneration of the first adsorbent, there is no need to use propene (ie, the second gas) for regeneration of the first adsorbent. As a result, the recovery amount and the recovery rate of the propene can be improved.

Further, by using the propane, which is not recovered as the product gas, for regeneration of the first adsorbent, a vacuum pump is not required for regeneration of the first adsorbent. For this reason, the power consumption and the facility maintenance costs can be kept low.

Furthermore, in the gas refining method of the present embodiment, the carbon dioxide can be sufficiently removed by the first adsorption tower, so that the purity of the propene is increased.

Second Embodiment

Figure 2:
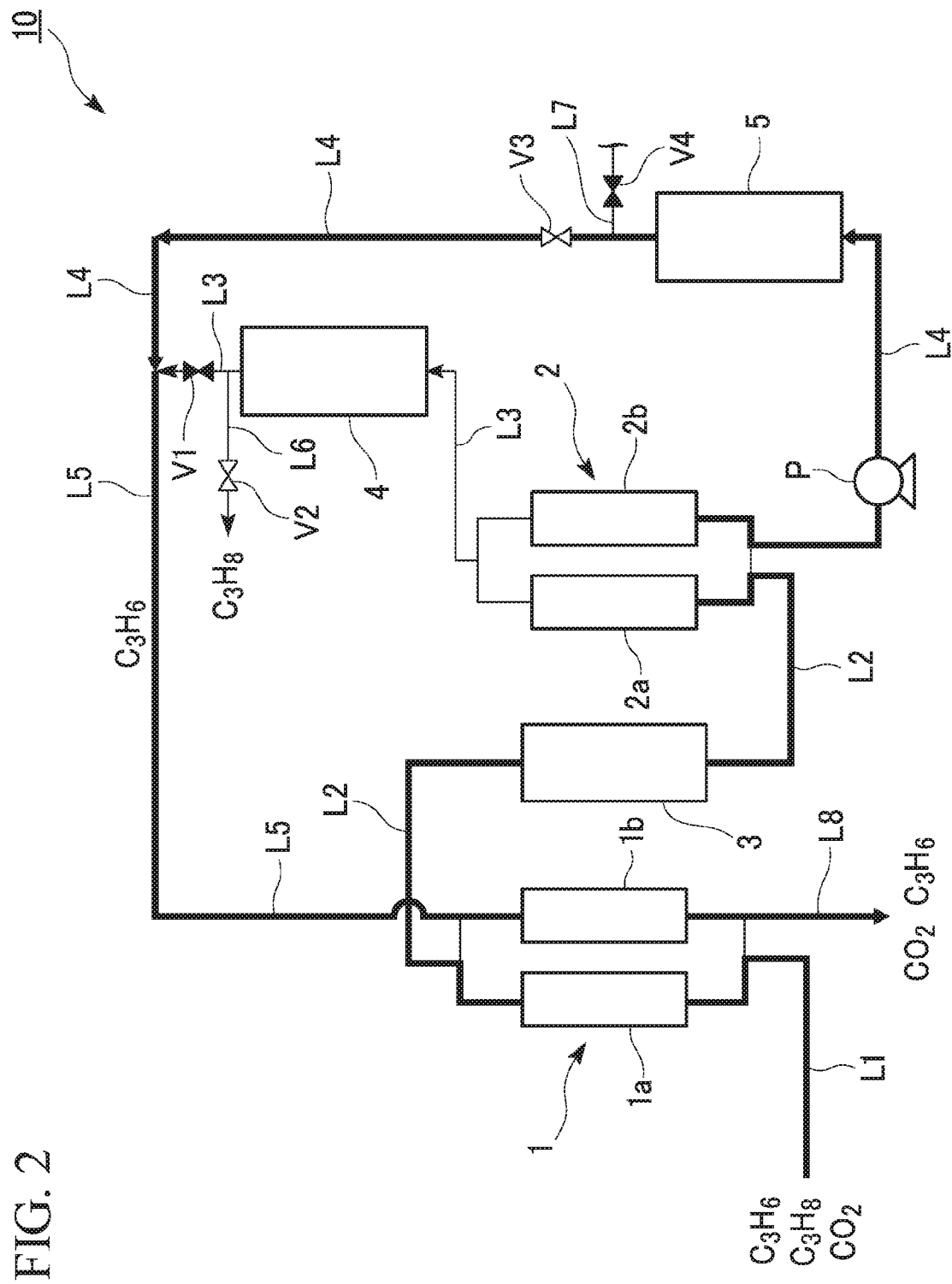
FIG. 2 is a schematic diagram for explaining a gas refining method of a second embodiment according to the present invention.

Hereinafter, the second embodiment will be described with reference to FIG. 2 as an example in which propane is recovered as the product gas. That is, in the second embodiment described below, the gas refining apparatus 10 is a propane manufacturing apparatus. In FIG. 2, a thick line means a line in which propene flows.

In the description of the second embodiment, the same configuration as the configuration described in the first embodiment is denoted by the same word and the same reference numeral, and the description is omitted.

As shown in FIG. 2, the on-off valve V2 and the on-off valve V3 are opened, and the on-off valve V1 and the on-off valve V4 are closed. In this state, the raw material gas is supplied into the first adsorption tower 1a, carbon dioxide is removed from the raw material gas in the first adsorption tower 1a, and propane and propene are separated from the carbon dioxide by the second adsorption tower 2a.

In the second embodiment, propane is recovered as the product gas from the first derivation line L3, propene is desorbed from the second adsorbent in the second adsorption tower 2b, and then introduced into the regeneration line L5 from the second derivation line L4.

That is, the propane separated by the second PSA unit 2 passes through the first derivation line L3 and the first recovery line L6 in this order and is recovered as the product gas. In addition, by introducing the propene from the second derivation line IA into the regeneration line L5, the propene can be used as the regeneration gas for the first adsorbent in the first adsorption tower 1b. As a result, carbon dioxide is desorbed from the first adsorbent in the first adsorption tower 1b, and gas containing propene and carbon dioxide flow through the regeneration exhaust gas line L8.

When desorbing the propene from the second adsorbent, it is preferable not to introduce propane from the second adsorption tower 2b into the second derivation line L4. As a result, the entire amount of the propane separated in the second PSA unit 2 can be recovered as it is, and the recovery amount and the recovery rate of the propane, which is the product gas, can be further increased. As a method of desorbing the propene from the second adsorbent, a method of using the pump P and sucking the inside of the second adsorption tower 2b through the second derivation line L4 is exemplified.

Effects

In the gas refining method of the second embodiment described above, propane is recovered as the product gas. Propene is not the product gas. By using propene (ie, the second gas) for regeneration of the first adsorbent, there is no need to use propane (ie, the first gas) for regeneration of the first adsorbent. As a result, the recovery amount and the recovery rate of the propane can be improved.

Further, in the gas refining method of the second embodiment, as in the first embodiment, the carbon dioxide can be sufficiently removed by the first adsorption tower, so that the purity of the propane is increased.

By using the propene, which is not recovered as the product gas, for regeneration of the first adsorbent, a vacuum pump is not required for regeneration of the first adsorbent. For this reason, the power consumption and the facility maintenance costs can be kept low.

As described above, according to the gas refining apparatus 10, it is possible to select either propane or propene and recover it as the product gas by a simple operation of switching the open/close state of the on-off valves V1 to V4.

Although several embodiments of the present invention have been described above, the present invention is not limited to such specific embodiments. In the present invention, additions, omissions, substitutions, and other modifications of the configuration may be added within the scope of the present invention described in the claims.

For example, in the above-described embodiments, the first adsorbent has been described as an example in which carbon dioxide can be adsorbed, and the second adsorbent has been described as an example in which propene can be adsorbed. However, the type and form of the first adsorbent and the second adsorbent can be appropriately selected according to the object to be removed in the raw material gas and the second gas.

Example

Hereinafter, the present invention will be specifically described by examples, but the present invention is not limited by the following description.

Example 1

In Example 1, propene was refined from a raw material gas by the PSA method using the gas refining apparatus 10, and propene was recovered as a product gas.

The raw material gas used in Example 1 contained 50% propane, 25% propene, and 25% carbon dioxide. The raw material gas was supplied into the first PSA unit 1 to remove carbon dioxide, and propane and propene were separated in the second PSA unit 2. For the regeneration of the first adsorbent, propane separated in the second PSA unit 2 was used.

Comparative Example 1

In Comparative Example 1, propene was recovered as a product gas in the same manner as in Example 1 except that a regeneration gas was not used during the regeneration of the first adsorbent, and the pressure in the first adsorption tower was reduced to atmospheric pressure.

Comparative Example 2

In Comparative Example 2, propene was recovered as a product gas in the same manner as in Example 1 except that gas used for the regeneration of the first adsorbent was changed to the gas in the first tank 3.

Reference Example 1

In Reference Example 1, propene was recovered as a product gas using gas refining apparatus provided with a vacuum pump in the regeneration exhaust gas line L8. In Reference Example 1, the vacuum pump was used without using a regeneration gas when regenerating the first adsorbent.

The compositions of the propene obtained in Example 1, Comparative Examples 1 and 2, and Reference Example 1 were analyzed, and the propene recovery rate, the removal rate of carbon dioxide, and the removal rate of propane were calculated. Table 1 shows these results.

TABLE 1

| | Use of vacuum pump | Regeneration gas for first adsorbent | Recovery rate of propene [%] | Removal rate of carbon dioxide [%] | Removal rate of propane [%] |
|---|---|---|---|---|---|
| Example 1 | none | propane | 91 | 93 | 91 |
| Comparative Example 1 | none | — | 69 | 37 | 70 |
| Comparative Example 2 | none | gas in first tank 3 | 51 | 92 | 89 |
| Reference Example 1 | presence | — | 90 | 94 | 92 |

In Example 1, the same recovery rates of propene, the same removal rate of carbon dioxide and propane could be achieved as those in Reference Example 1, which is an example using a vacuum pump. That is, in Example 1, propene could be manufactured with a method which was inexpensive as compared with the case in which a vacuum pump was used, and with the same purity and the same recovery rate as those in a case of using a vacuum pump.

In Comparative Example 1, the pressure in the first adsorption tower was reduced to the atmospheric pressure without using the regeneration gas during the regeneration of the first adsorbent. For this reason, the regeneration of the first adsorbent was insufficient, and the removal rate of carbon dioxide was reduced. As a result, the recovery rate of propene was reduced.

In Comparative Example 2, since the gas in the first tank 3 was used for the regeneration of the first adsorbent, the recovery rate of propene was reduced.

EXPLANATION OF REFERENCE NUMERAL

1 first PSA unit
2 second PSA unit
1a, 1b first adsorption tower
2a, 2b second adsorption tower
3 first tank
4 second tank
5 third tank
10 gas refining apparatus
L1 raw material line
L2 connection line
L3 first derivation line
L4 second derivation line
L5 regeneration line
L6 first recovery line
L7 second recovery line
L8 regeneration exhaust gas line
P pump
V1-V4 on-off valve

The invention claimed is:

1. A gas refining apparatus for refining a product gas from a raw material gas containing a first gas and a second gas by a pressure swing adsorption method,
wherein the gas refining apparatus comprises:
a first adsorption tower having a first adsorbent for adsorbing gas other than the first gas and the second gas;
a second adsorption tower having a second adsorbent for adsorbing the second gas;
a connection line which connects a secondary side of the first adsorption tower and a primary side of the second adsorption tower, and through which the first gas and the second gas flow;
a first derivation line connected to a secondary side of the second adsorption tower and through which the first gas flows;
a second derivation line connected to the primary side of the second adsorption tower and through which the second gas flows;
a regeneration line connected to the secondary side of the first adsorption tower and through which a regeneration gas for regenerating the first adsorbent flows; and
a suction apparatus provided in the second derivation line and configured to desorb the second gas from the second adsorbent,
wherein the regeneration line is connected to each of the first derivation line and the second derivation line,
wherein the first derivation line is configured to introduce the first gas from the secondary side of the second adsorption tower into the regeneration line, and
wherein the second derivation line is configured to introduce the second gas from the primary side of the second adsorption tower into the regeneration line.

2. The gas refining apparatus according to claim 1,
wherein the gas refining apparatus further comprises a first recovery line branched from the first derivation line, and a second recovery line branched from the second derivation line,
an on-off valve is provided in each of the first derivation line, the second derivation line, the first recovery line, and the second recovery line, and
by switching an open/close state of the on-off valve, one of the first gas and the second gas is selected and recovered as the product gas.

3. A gas refining method by a pressure swing adsorption system using the gas refining apparatus according to claim 1,
wherein the gas refining method comprises:
a step of causing the first adsorbent to adsorb gas other than the first gas and the second gas, which is contained in the raw material gas;
a step of supplying the first gas and the second gas from the first adsorption tower into the second adsorption tower;
a step of adsorbing the second gas on the second adsorbent, then desorbing the second gas from the second adsorbent, and recovering the second gas desorbed from the second adsorbent as the product gas through the second derivation line; and
a step of introducing the first gas from the first derivation line into the regeneration line.

4. A gas refining method by a pressure swing adsorption system using the gas refining apparatus according to claim 1,
wherein the gas refining method comprises:
a step of causing the first adsorbent to adsorb a gas other than the first gas and the second gas, which is contained in the raw material gas;
a step of supplying the first gas and the second gas from the first adsorption tower into the second adsorption tower;

a step of adsorbing the second gas on the second adsorbent, then recovering the first gas as the product gas through the first derivation line; and a step of desorbing the second gas from the second adsorbent and introducing the second gas desorbed from the second adsorbent from the second derivation line into the regeneration line.

5. A gas refining method by a pressure swing adsorption system using the gas refining apparatus according to claim 2, wherein the gas refining method comprises:

a step of causing the first adsorbent to adsorb gas other than the first gas and the second gas, which is contained in the raw material gas;

a step of supplying the first gas and the second gas from the first adsorption tower into the second adsorption tower;

a step of adsorbing the second gas on the second adsorbent, then desorbing the second gas from the second adsorbent, and recovering the second gas desorbed from the second adsorbent as the product gas through the second derivation line; and a step of introducing the first gas from the first derivation line into the regeneration line.

6. A gas refining method by a pressure swing adsorption system using the gas refining apparatus according to claim 2, wherein the gas refining method comprises:

a step of causing the first adsorbent to adsorb a gas other than the first gas and the second gas, which is contained in the raw material gas;

a step of supplying the first gas and the second gas from the first adsorption tower into the second adsorption tower;

a step of adsorbing the second gas on the second adsorbent, then recovering the first gas as the product gas through the first derivation line; and a step of desorbing the second gas from the second adsorbent and introducing the second gas desorbed from the second adsorbent from the second derivation line into the regeneration line.

7. A propene manufacturing apparatus which produces propene from a raw material gas containing propane and propene by a pressure swing adsorption method, wherein the propene manufacturing apparatus comprises:

a first adsorption tower having a first adsorbent for adsorbing gas other than propane and propene;

a second adsorption tower having a second adsorbent for adsorbing propene;

a connection line which connects a secondary side of the first adsorption tower and a primary side of the second adsorption tower, and through which propane and propene flow;

a first derivation line connected to a secondary side of the second adsorption tower and through which propane flows;

a second derivation line connected to the primary side of the second adsorption tower and through which propene flows;

a regeneration line connected to the secondary side of the first adsorption tower and through which a regeneration gas for regenerating the first adsorbent flows; and a suction apparatus provided in the second derivation line and configured to desorb propene from the second adsorbent, wherein the regeneration line is connected to each of the first derivation line and the second derivation line, and wherein propane is introduced from the first derivation line into the regeneration line and propene is recovered from the second derivation line.

8. A propane manufacturing apparatus which produces propane from a raw material gas containing propane and propene by a pressure swing adsorption method, wherein the propane manufacturing apparatus comprises:

a first adsorption tower having a first adsorbent for adsorbing gas other than propane and propene;

a second adsorption tower having a second adsorbent for adsorbing propene;

a connection line which connects a secondary side of the first adsorption tower and a primary side of the second adsorption tower, and through which propane and propene flow;

a first derivation line connected to a secondary side of the second adsorption tower and through which propane flows;

a second derivation line connected to the primary side of the second adsorption tower and through which propene flows;

a regeneration line connected to the secondary side of the first adsorption tower and through which a regeneration gas for regenerating the first adsorbent flows; and a suction apparatus provided in the second derivation line and configured to desorb propene from the second adsorbent, wherein the regeneration line is connected to each of the first derivation line and the second derivation line, and wherein propene is introduced from the second derivation line into the regeneration line and propane is recovered from the first derivation line.

\* \* \* \* \*